//  US007504552B2

United States Patent
Tamura et al.

(10) Patent No.: US 7,504,552 B2
(45) Date of Patent: Mar. 17, 2009

(54) ABSORBENT ARTICLE WITH COMPRESSED GROOVE AND FLEXIBLE PORTION

(75) Inventors: Tatsuya Tamura, Kagawa (JP); Satoshi Mizutani, Mitoyo-gun (JP); Makoto Suekane, Kagawa (JP); Shimpei Komatsu, Kagawa (JP)

(73) Assignee: Uni-Charm Corporation, Ehime-Ken (JP)

( * ) Notice: Subject to any disclaimer, the term of this patent is extended or adjusted under 35 U.S.C. 154(b) by 108 days.

(21) Appl. No.: 10/530,292

(22) PCT Filed: Dec. 24, 2003

(86) PCT No.: PCT/JP03/16557

§ 371 (c)(1),
(2), (4) Date: Apr. 4, 2005

(87) PCT Pub. No.: WO2004/060253

PCT Pub. Date: Jul. 22, 2004

(65) Prior Publication Data

US 2006/0100598 A1 May 11, 2006

(30) Foreign Application Priority Data

Dec. 27, 2002 (JP) ............................. 2002-381564

(51) Int. Cl.
*A61F 13/15* (2006.01)
*A61F 13/20* (2006.01)
(52) U.S. Cl. ............ 604/380; 604/385.01; 604/385.101
(58) Field of Classification Search .... 604/378–385.01, 604/385.101
See application file for complete search history.

(56) References Cited

U.S. PATENT DOCUMENTS

| 4,059,114 | A | * | 11/1977 | Richards ................... 604/359 |
| 4,333,466 | A | | 6/1982 | Matthews |
| 5,795,345 | A | * | 8/1998 | Mizutani et al. ............. 604/380 |
| 5,830,296 | A | * | 11/1998 | Emenaker et al. ........... 156/219 |
| 6,312,416 | B1 | * | 11/2001 | Brisebois et al. ........ 604/385.01 |
| 6,953,451 | B2 | * | 10/2005 | Berba et al. ............ 604/385.01 |
| 2001/0007065 | A1 | * | 7/2001 | Blanchard et al. ............ 604/369 |

FOREIGN PATENT DOCUMENTS

| JP | H03-33622 | 4/1991 |
| JP | 10-272156 | 10/1998 |
| JP | 10-328233 | 12/1998 |

* cited by examiner

*Primary Examiner*—Michele Kidwell
(74) *Attorney, Agent, or Firm*—Darby & Darby P.C.

(57) ABSTRACT

Disclosed is an absorbent article including compressed grooves (11) and a rear flexible portion (16). The compressed grooves (11) where a liquid absorbent layer (4) is compressed and recessed from the side of a skin surface toward a garment surface are provided to extend in a longitudinal direction of the article so as to approach each other the nearest on a lateral reference line (Ox-Ox) of the article. The rear flexible portion (16) where the liquid absorbent layer (4) is recessed from the side of the garment surface toward the skin surface is provided to extend toward a rear end edge (1d) from a starting point (16a) that is located closer to the rear end edge (1d) than the lateral reference line (Ox-Ox). At least a portion of the rear flexible portion (16) is located between the compressed grooves (11).

5 Claims, 8 Drawing Sheets

ABSORBENT ARTICLE WITH COMPRESSED GROOVE AND FLEXIBLE PORTION

CROSS REFERENCE TO THE RELATED APPLICATION

The present application has been filed with claiming priority based on Japanese Patent Application No. 2002-381564, filed on Dec. 27, 2002. Disclosure of the above-identified Japanese Patent Application is herein incorporated by reference.

TECHNICAL FIELDS

The present invention relates to an absorbent article suitable for absorbing menstrual blood and so on discharged from a woman's genital organ, more particularly, relates to an absorbent article that can easily conform to the vaginal opening and the cleft of the buttocks.

BACKGROUND ART

Absorbent articles intended to absorb menstrual blood discharged from a woman's genital organ are typically constructed to include a liquid absorbent layer, a liquid-permeable topsheet covering the skin surface of the liquid absorbent layer, and a liquid-impermeable backsheet covering the garment surface of the liquid absorbent layer, and generally, they are worn with the backsheet adhered to an inner side of a groin piece of an undergarment through a pressure-sensitive adhesive layer.

Generally, an undergarment to be worn by a woman at the period of menstruation can tightly constrict the wearer's body so as to bring the absorbent article into close contact with the wearer's crotch. However, such a tight undergarment may possibly make the wearer feel unpleasant due to excessive pressure on her lower body during wear. This is noticeable in a hot and humid environment such as summer.

Accordingly, it is required not only that the absorbent article to be used at the period of menstruation come into close contact with the wearer's body by a tightening force from the undergarment but also that the absorbent article be so constructed as to be easily deformed by a force that will be applied from the thighs when put in the wearer's crotch for coming into close contact with the vaginal opening and so on.

Japanese Unexamined Utility-Model Publication No. 3-33622 (Patent Publication 1) discloses an absorbent article that can be easily deformed to come into close contact with the vaginal opening.

In this absorbent article, topside compressed grooves are formed in two sides of its skin surface intended to face the wearer's body, while a backside compressed groove is formed in its garment surface intended to face an undergarment to extend rearwardly from the center of the absorbent article at an intermediate position between the topside compressed grooves. When the absorbent article is applied to the wearer's crotch and the wearer's thighs exert a pressure toward the center of the absorbent article, the absorbent article can be deformed such that its central portion is folded at the backside compressed groove to bulge toward the wearer's body with the topside compressed grooves functioning as starting points, whereby the central portion easily comes into close contact with the vaginal opening.

Such an absorbent article having grooves formed in both the skin surface and the garment surface is also disclosed in Japanese Unexamined Patent Publication No. 10-328233 (Patent Publication 2). This absorbent article suitable for nighttime use is elongated and slightly widened at its rear portion. In this absorbent article, topside grooves are formed in the skin surface at two sides of a portion that is intended to face the vaginal opening; and a rear groove is formed in the garment surface while being located rearwardly apart from the topside grooves. With the rear groove provided in a rear portion of the garment surface, the absorbent article applied to the wearer's crotch can be easily deformed to bulge so that its portion having the rear groove can fit in the cleft of the buttocks.

In the absorbent article disclosed in Patent Publication 1, however, the backside compressed groove formed in the garment surface extends at some length rearwardly from the center of the absorbent article. When applied to the wearer's crotch and subjected to a pressure from the thighs, therefore, the absorbent article bulges toward the wearer's body over almost the whole length. Since the absorbent article is so constructed as to be easily folded to decrease its width over almost the whole length, the absorbent article in a folded state is hardly restored to its original flat state, so that the absorbent article cannot be certainly kept in close contact with the vaginal opening and the cleft of the buttocks. Accordingly, it may possibly fail to collect menstrual blood, causing lateral leakage or rearward leakage.

In addition, since the backside compressed groove extends rearwardly from the center of the absorbent article, if the absorbent article is accidentally worn back to front to have its front portion not having the backside compressed groove opposed to the cleft of the buttocks, the absorbent article cannot closely fit into the cleft of the buttocks.

In the absorbent article disclosed in Patent Publication 1, furthermore, since pressure-sensitive adhesive layers for adhering the article to an undergarment are provided only in its front portion, it may possibly be adhered to an undergarment with its rear portion curled up or folded back.

In the elongated absorbent article disclosed in Patent Publication 2, on the other hand, the topside grooves on the skin surface are not located at two sides of the rear groove that is provided in the rear portion of the article. Therefore, pressure acting on the topside grooves from the thighs cannot be transmitted to the rear groove, so that it is difficult to deform the portion having the rear groove to bulge toward the cleft of the buttocks only by pressure from the thighs. That is, this absorbent article is designed to be used in combination with a tight undergarment that is provided centrally of its back body with an elastic member or the like for exerting a strong tightening force on the rear portion of the absorbent article. Accordingly, if a relatively loose undergarment is worn, the portion having the rear groove will be hardly deformed to bulge toward the cleft of the buttocks.

The present invention has been worked out in view of the shortcomings in the prior art set forth above. It is therefore an object of the present invention to provide an absorbent article which can be easily brought into close contact with an area from the vaginal opening to the cleft of the buttocks, wherein when applied a pressure from the thighs, the absorbent article can be locally deformed to bulge toward the cleft of the buttocks without being folded back as a whole.

DISCLOSURE OF THE INVENTION

According to the present invention, there is provided an absorbent article comprising a liquid absorbent layer, the absorbent article having a skin surface and a garment surface, wherein compressed grooves where the liquid absorbent layer is compressed and recessed from the side of the skin surface toward the garment surface are provided to extend in a longitudinal direction of the article, the compressed grooves being located laterally apart from a longitudinal centerline of the article, a separation distance between the compressed grooves being smallest on a lateral reference line of the article or within a range of an equal distance forward and rearward from the lateral reference line in the longitudinal direction, wherein a rear flexible portion where the liquid absorbent layer is recessed from the side of the garment surface toward the skin surface is provided to extend toward a rear end edge of the article from a starting point that is located closer to the rear end edge than the lateral reference line, at least a portion of the rear flexible portion being located between the compressed grooves.

When a pressure acts on the compressed grooves from the thighs, since the rear flexible portion does not overlap with the lateral reference line that is intended to face the vaginal opening of a wearer, the absorbent article can be pressed against the wearer's vaginal opening without being sharply bent at its portion intended to face the vaginal opening. In its rear portion, on the other hand, since at least a portion of the rear flexible portion is located between the compressed grooves, the portion having the rear flexible portion can be bent to fit into the cleft of the buttocks by the pressure acting on the compressed grooves from the thighs. Accordingly, even if a relatively loose undergarment is worn, the absorbent article can be brought into close contact not only with the vaginal opening but also with the cleft of the buttocks by the pressure from the thighs.

In the present invention, the absorbent article may also be provided with a front flexible portion similar in structure to the rear flexible portion, wherein the front flexible portion extends toward a front end edge of the article from a starting point that is located closer to the front end edge than the lateral reference line, and at least a portion of the front flexible portion is located between the compressed grooves. In this case, it is preferred that the front and rear end edges are located an equal distance apart from the lateral reference line, and the front and rear flexible portions are also located an equal distance apart from the lateral reference line. Here, it is more preferred that the compressed grooves and the front and rear flexible portions are formed in a pattern symmetrical about the lateral reference line.

If the absorbent article is of symmetrical configuration about the lateral reference line, as set forth above, one of the two flexible portions can be opposed to the cleft of the buttocks without fail, regardless of which one of longitudinally opposed end edges is directed forward when the absorbent article is worn.

Within a range of an equal distance forward and rearward from the lateral reference line in the longitudinal direction, additional compressed grooves may be provided side by side with the compressed grooves.

If two grooves in a side-by-side relationship are provided on each side of the article within the above-mentioned range, preferably within a range not overlapping with the flexible portion, stiffness can be increased at right and left sides of the portion intended to face the vaginal opening, so that when a pressure from the thighs is exerted thereon, the portion can be easily pressed against the vaginal opening.

In the present invention, it is also preferred that a mean thickness of the absorbent article at both sides of the rear flexible portion is smaller than that at a region extending an equal distance forward and rearward from lateral reference line in the longitudinal direction but not overlapping with the rear flexible portion.

In this construction, since the portion having the rear flexible portion becomes relatively thin to have a low basis weight, this portion can be easily bent to bulge toward the cleft of the buttocks. On the other hand, since the portion intended to face the vaginal opening becomes relatively thick to have a high basis weight, this portion can be certainly pressed against the vaginal opening without causing bending deformation.

It is also preferred that pressure-sensitive adhesive layers for adhering the article to an undergarment are disposed on the garment surface, the pressure-sensitive adhesive layers being located laterally apart from the longitudinal centerline and present at least on the lateral reference line and on both sides of the rear flexible portion.

In this construction, since the absorbent article can be firmly fixed to an undergarment at both sides of the portion intended to face the vaginal opening and at both sides of the rear flexible portion through the pressure-sensitive adhesive layers, a shrinkage force of the undergarment certainly acts on the absorbent article in the vicinity of the lateral reference line, so that the portion along the lateral reference line can be easily brought into close contact with the vaginal opening. In addition, since the absorbent article can be firmly fixed to an undergarment at both sides of the rear flexible portion, the portion having the rear flexible portion can always remain opposed to the cleft of the buttocks without being displaced from the undergarment.

BRIEF DESCRIPTION OF THE DRAWINGS

The present invention will be understood more fully from the detailed description given hereinafter and from the accompanying drawings of the preferred embodiments of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

In the present invention, the absorbent article refers to devices which are intended to be worn in the crotch of a wearer to absorb various exudates discharged from the wearer's body, such as menstrual blood, urine, and vaginal discharge, but in the following embodiments, the absorbent article is shown embodied in a sanitary napkin whose primary object is to absorb menstrual blood discharged from the vaginal opening of a woman. It should be noted that the absorbent article has two major surfaces: of which one surface intended to be worn toward the wearer's crotch is referred to as "skin surface", while the other surface is referred to as "garment surface" regardless of whether a garment is worn outside the absorbent article or not.

As used herein, the term "compressed groove" refers to a groove where at least the liquid absorbent layer is highly compressed from the side of the skin surface toward the garment surface. In each compressed groove that is formed to extend continuously, density of the liquid absorbent layer may be uniform at the groove bottom or portions of different densities may alternate with each other at the groove bottom. In either case, the density of the liquid absorbent layer is higher at the bottom of the compressed groove than at regions other than the compressed groove. On the other hand, the term "flexible portion" refers to a portion where the liquid absorbent layer is compressed from the side of the garment surface toward the skin surface or a portion where the thickness of the liquid absorbent layer is reduced to have a lower basis weight than portions other than the flexible portion. Preferably, the flexible portion is brought into coincidence with or positioned in the vicinity of the longitudinal centerline of the absorbent article. For example, it is preferred that the flexible portion is not located more than 10 mm apart from the longitudinal centerline.

As used herein, the term "longitudinal centerline" refers to a line which extends longitudinally to divide the absorbent article laterally in two. On the other hand, the term "lateral reference line" refers to a lateral centerline which extends laterally to divide the absorbent article longitudinally in two, when the absorbent article is of symmetrical configuration about the lateral reference line. However, the absorbent article may be asymmetrical about the lateral reference line. In either case, the lateral reference line as used herein is located at a position where the separation distance between right and left compressed grooves becomes smallest. In the case where the right and left compressed grooves are arranged to provide the smallest separation distance over a region of a given length in the longitudinal direction, the lateral reference line refers to a line which extends laterally to divide this region longitudinally in two.

Figure 1:
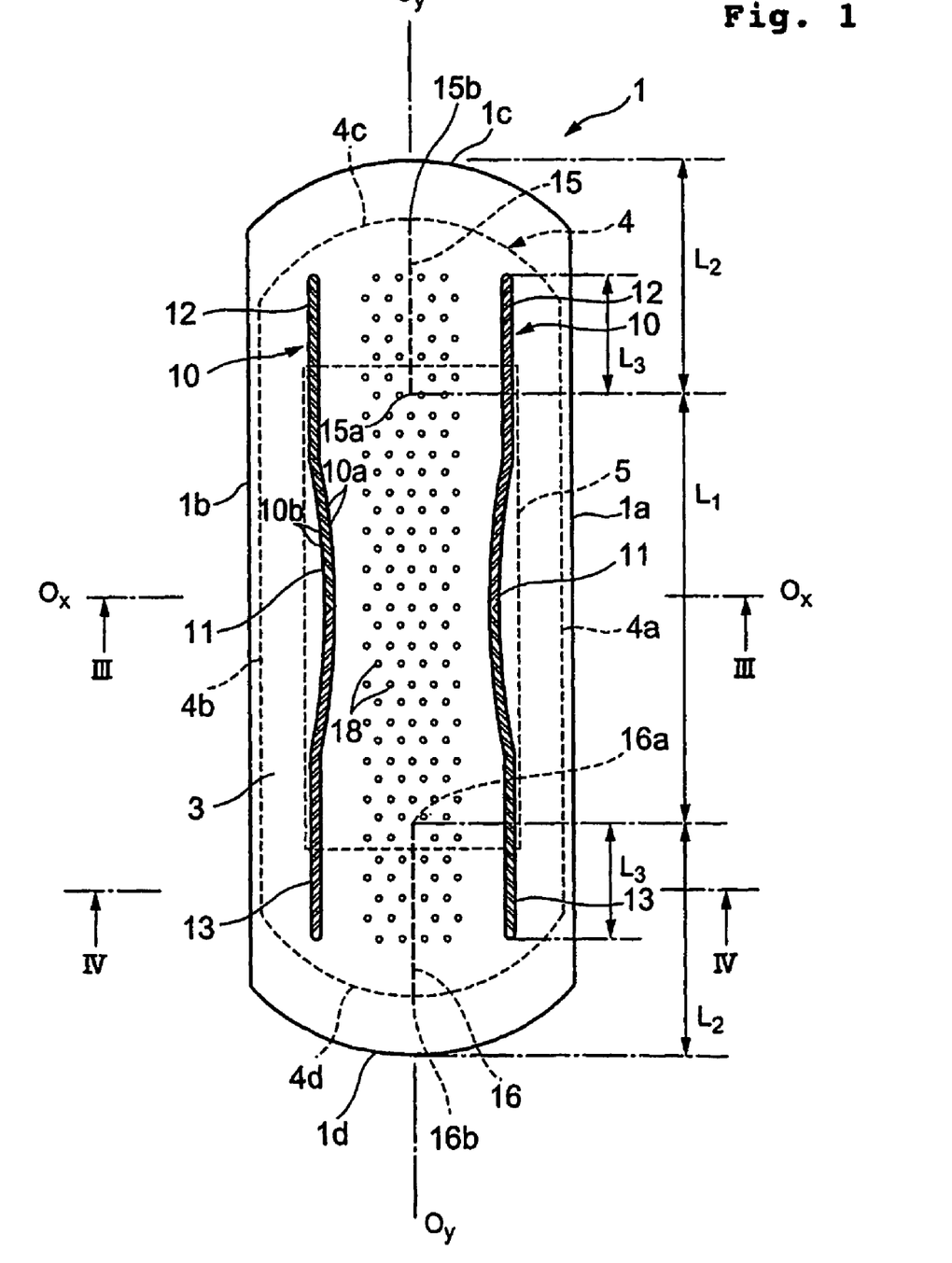
FIG. 1 is a top plan view showing a sanitary napkin as an absorbent article according to a first embodiment of the present invention.
Figure 2:
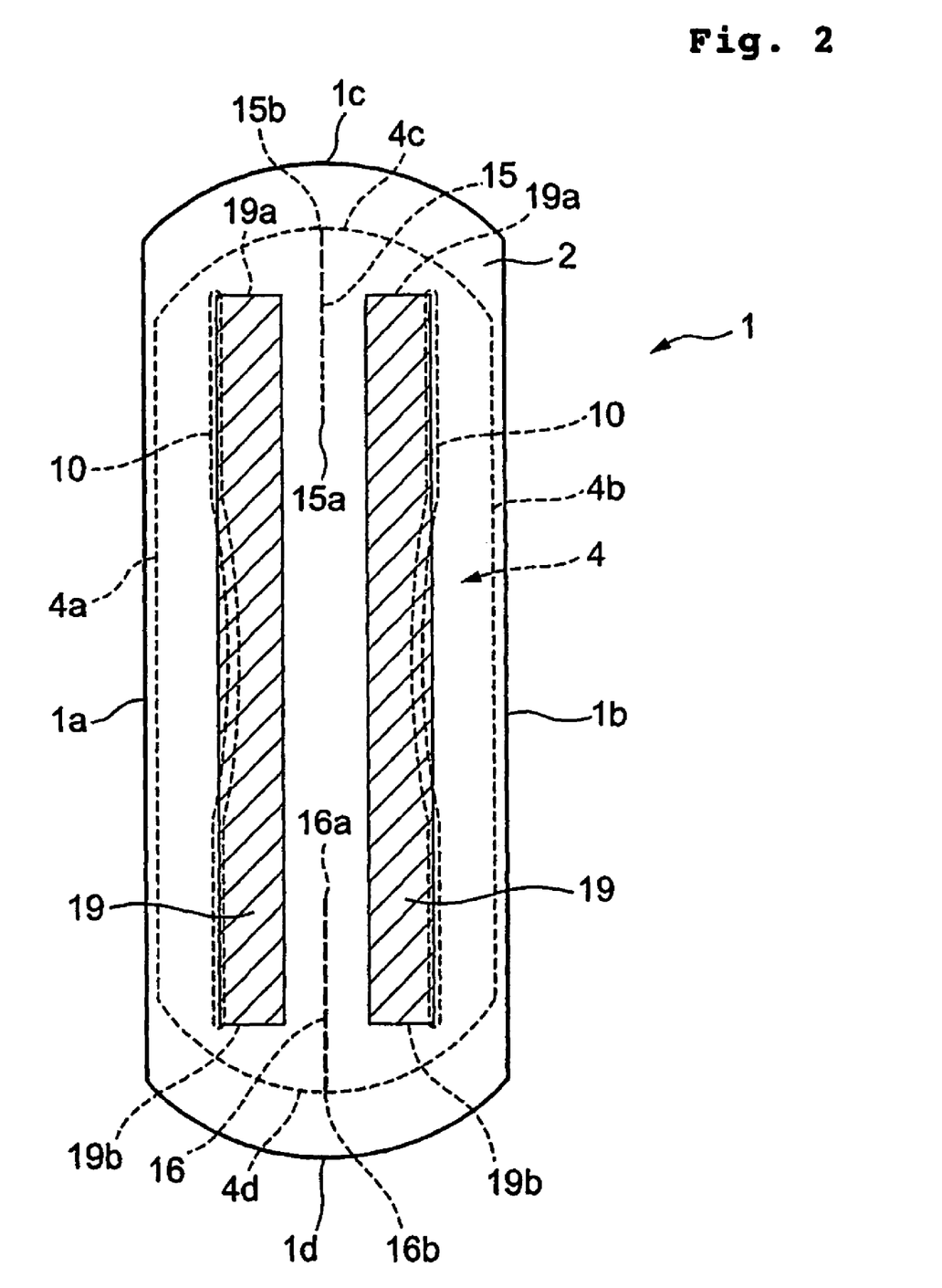
FIG. 2 is a bottom plan view showing the sanitary napkin according to the first embodiment.
Figure 3:
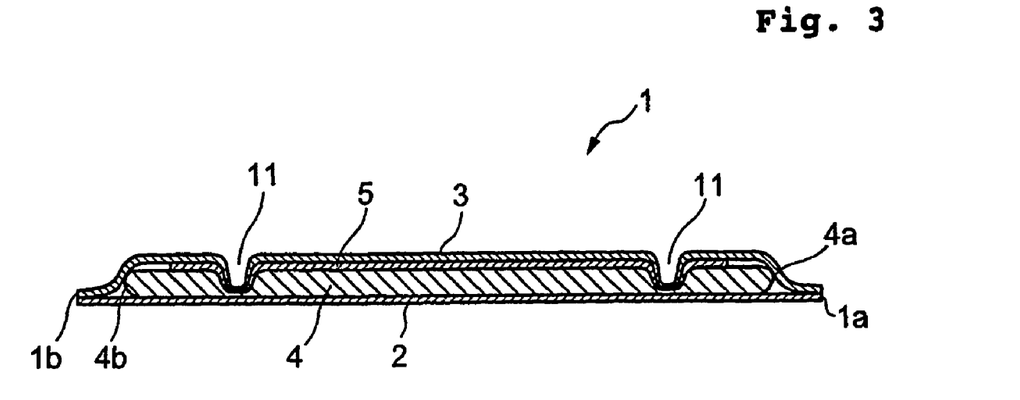
FIG. 3 is a sectional view of the sanitary napkin taken along line III-III of FIG. 1.

FIG. 1 is a top plan view showing a sanitary napkin 1 as an absorbent article according to a first embodiment of the present invention, wherein the skin surface faces upward; FIG. 2 is a bottom plan view showing the sanitary napkin 1 of FIG. 1, wherein the garment surface faces upward; FIG. 3 is a sectional view of the sanitary napkin 1 taken along line III-III of FIG. 1; and FIG. 4 is a sectional view of the sanitary napkin 1 taken along line IV-IV of FIG. 1.

The sanitary napkin 1 shown in FIG. 1 is of symmetrical configuration about the longitudinal centerline Oy-Oy and also about the lateral reference line Ox-Ox. Therefore, the sanitary napkin 1 has no difference between front and rear, so that it can be used in the same manner regardless of which one of longitudinally opposed end edges is directed to the abdomen. In the following description, however, one of the longitudinally opposed end edges is referred to as front end edge 1c while the other is referred to as rear end edge 1d, for convenience of explanation, wherein the side of the front end edge 1c is called front side while the opposite side of the rear end edge 1d is called rear side.

The sanitary napkin 1 has right and left longitudinally extending side edges 1a and 1b that are laterally located an equal distance apart from the longitudinal centerline Oy-Oy. The front and rear end edges 1c and 1d are outwardly curved and longitudinally located an equal distance apart from the lateral reference line Ox-Ox.

Figure 4:
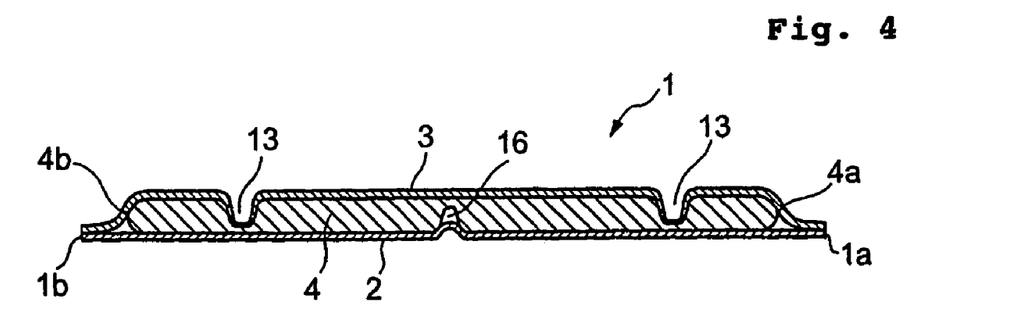
FIG. 4 is a sectional view of the sanitary napkin taken along line IV-IV of FIG. 1.

As shown in the respective sectional views of FIGS. 3 and 4, the sanitary napkin 1 has a liquid-impermeable backsheet 2 appearing on its garment surface and a liquid-permeable topsheet 3 appearing on its skin surface. Between the backsheet 2 and the topsheet 3, there is disposed a first liquid absorbent layer 4. As indicated by a dotted line in FIG. 1, the first liquid absorbent layer 4 has right and left side edges 4a and 4b that are located inwardly apart from the right and left side edges 1a and 1b, respectively. The first liquid absorbent layer 4 also has front and rear end edges 4c and 4d that are located inwardly apart from the front and rear end edges 1c and 1d, respectively.

Between the topsheet 3 and the first liquid absorbent layer 4, there is further provided a second liquid absorbent layer 5. As shown in FIG. 1, the second liquid absorbent layer 5 is rectangular in plan configuration and provided only centrally of the sanitary napkin 1. In the present embodiment, the liquid absorbent layer refers to both the first liquid absorbent layer 4 and the second liquid absorbent layer 5. In the liquid absorbent layer composed of the first liquid absorbent layer 4 and the second liquid absorbent layer 5, as will be described later, the basis weight and the density are different for different portions.

Although omitted from the drawings, a second sheet is provided beneath the topsheet 3. This second sheet is located at least beneath a region over which liquid passage holes 18 are distributed. In the sanitary napkin 1, the topsheet 3, the second sheet, the second liquid absorbent layer 5 and the first liquid absorbent layer 4 are locally heated under pressure to form compressed grooves 10, 10 in the skin surface. In regions where neither the second sheet nor the second liquid absorbent layer 5 is present, of course, the topsheet 3 and the first liquid absorbent layer 4 are locally heated under pressure to form the compressed grooves 10, 10.

These compressed grooves 10, 10 are formed by embossing with a heating roller, wherein after the topsheet 3, the second sheet, the second liquid absorbent layer 5 and the first liquid absorbent layer 4 are stacked, a smooth surface roller is applied to an exterior surface of the first liquid absorbent layer 4 while a heating roller having projections arranged in a pattern for embossing is applied to a surface of the topsheet 3 for pressing and heating.

At the bottoms of the compressed grooves 10, 10, there are provided high-density compressed portions 10a, in which materials are pressed until they get almost filmy, and medium-density compressed portions 10b positioned between adjacent high-density compressed portions 10a, in which although doesn't get filmy, the material is of a higher density than in portions other than the compressed groove 10. The high-density compressed portions 10a and the medium-density compressed portions 10b alternate with each other all along the compressed grooves 10, 10, providing continuous grooves where the skin surface of the sanitary napkin 1 is recessed toward the side of the backsheet 2.

The compressed grooves 10, 10 are extended in the longitudinal direction and laterally located an equal distance apart from the longitudinal centerline Oy-Oy. That is, the compressed grooves 10, 10 are of symmetrical configuration about the longitudinal centerline Oy-Oy. In addition, the individual compressed grooves 10 are of symmetrical configuration about the lateral reference line Ox-Ox.

The compressed grooves 10, 10 include: first compressed portions 11, 11 provided within a range of an equal distance forward and rearward from the lateral reference line Ox-Ox in the longitudinal direction; second compressed portions 12, 12 extending forward from the first compressed portions 11, 11 without interruption; and third compressed portions 13, 13 extending rearward from the first compressed portions 11, 11 without interruption.

In the embodiment shown in FIG. 1, the first compressed portions 11, 11 are curved toward the longitudinal centerline Oy-Oy, wherein the separation distance between the first compressed portions 11, 11 becomes smallest at intersections with the lateral reference line Ox-Ox and gradually increases away from the lateral reference line Ox-Ox in the longitudinal direction. Alternatively, the separation distance between the first compressed portions 11, 11 may be kept smallest over a given length in the longitudinal direction. In this case, the lateral reference line Ox-Ox is located at the longitudinal center of the length over which the smallest separation distance is kept.

The second compressed portions 12, 12 extend parallel with each other as well as with the longitudinal centerline Oy-Oy. Likewise, the third compressed portions 13, 13 extend parallel with each other as well as with the longitudinal centerline Oy-Oy. The separation distance between the second compressed portions 12, 12 is equal to that between the third compressed portions 13, 13, so that the separation distance between the compressed grooves 10, 10 becomes largest in between the second compressed portions 12, 12 and in between the third compressed portions 13, 13.

As shown in FIGS. 1 and 2, front and rear flexible portions 15 and 16 are located an equal distance apart from the lateral reference line Ox-Ox forward and rearward in the longitudinal direction. As shown in FIG. 4, the flexible portions 15 and 16 are formed by recessing the first liquid absorbent layer 4 from the side of the garment surface toward the skin surface so as to extend along the longitudinal centerline Oy-Oy. Preferably, the flexible portions 15 and 16 are brought into coincidence with the longitudinal centerline Oy-Oy. Alternatively, the flexible portions 15 and 16 may be positioned in the vicinity of the longitudinal centerline Oy-Oy so as not to be located more than 10 mm apart from the longitudinal centerline Oy-Oy in the lateral direction. The flexible portions 15 and 16 may be formed by pressing the first liquid absorbent layer 4 between two rollers such that a smooth surface roller is applied to an upper surface (skin surface) of the first liquid absorbent layer 4 while a roller having linearly extending projections is applied to its lower surface (garment surface). These rollers may be at room temperature or may be heated.

Alternatively, the flexible portions 15 and 16 may be formed by locally reducing the thickness of the first liquid absorbent layer 4 to have a low basis weight. The individual flexible portions 15 and 16 may be composed of two or more separate parts. For example, the individual flexible portions 15 and 16 may be composed of two separate grooves that are positioned at two sides of the longitudinal centerline Oy-Oy to extend parallel with the longitudinal centerline Oy-Oy.

The flexible portion 15 has a starting point 15a and the flexible portion 16 has a starting point 16a, wherein the starting point 15a and the starting point 16a are located an equal distance apart from the lateral reference line Ox-Ox forward and rearward in the longitudinal direction. It should be noted that the starting point 15a and the starting point 16a are positioned forward of and rearward of the first compressed portions 11, 11, respectively, without overlapping with the first compressed portions 11, 11 as viewed from the lateral direction. On the other hand, the flexible portion 15 has an endpoint 15b coinciding with the front end edge 4c of the first liquid absorbent layer 4 and the flexible portion 16 has an end point 16b coinciding with the rear end edge 4d of the first liquid absorbent layer 4. Thus, the flexible portions 15 and 16 are symmetrical to each other about the lateral reference line Ox-Ox.

In the present embodiment, the individual flexible portions 15 and 16 are formed to extend in the shape of a continuous line from the starting point 15a or 16a to the end point 15b or 16b. Alternatively, the individual flexible portions 15 and 16 may be formed such that discrete recesses are arranged at intervals from the starting point 15a or 16a to the end point 15b or 16b.

As shown in FIGS. 1 and 2, the flexible portion 15 is inserted between the second compressed portions 12, 12, wherein the length L3 over which the flexible portion 15 overlaps with the second compressed portions 12 as viewed from the lateral direction is preferably equal to or greater than 10 mm. Similarly, the flexible portion 16 is inserted between the third compressed portions 13, 13, wherein the length L3 over which the flexible portion 16 overlaps with the third compressed portions 13 as viewed from the lateral direction is preferably equal to or greater than 10 mm. More preferably, the length L3 is equal to or greater than 15 mm.

In the sanitary napkin 1, the range of length L1 between the starting point 15a of the flexible portion 15 and the starting point 16a of the flexible portion 16 is referred to as central portion, the range of length L2 between the starting point 15a and the front end edge 1c is referred to as front portion, and the range of length L2 between the starting point 16a and the rear end edge 1d is referred to as rear portion.

As shown in FIG. 1, a large number of liquid passage holes 18 are formed in the skin surface of the sanitary napkin 1 within a region located between the compressed grooves 10, 10. In the portion having the second sheet, the liquid passage holes 18 are formed to pass through both the topsheet 3 and the second sheet. In the portion not having the second sheet, on the other hand, the liquid passage holes 18 are formed to pass through only the topsheet 3.

It should be noted that the stack of the topsheet 3 and the second sheet is bonded to the second liquid absorbent layer 5, the first liquid absorbent layer 4 and the backsheet 2 through a hot-melt type adhesive. The first liquid absorbent layer 4 is also bonded to the backsheet 2 through a hot-melt type adhesive.

On the garment surface of the sanitary napkin 1, i.e., on the exterior surface of the backsheet 2, as shown in FIG. 2, there are disposed pressure-sensitive adhesive layers 19, 19. The pressure-sensitive adhesive layers 19, 19 are laterally located an equal distance apart from the longitudinal centerline Oy-Oy. The pressure-sensitive adhesive layers 19, 19 should be present at least on the lateral reference line Ox-Ox and on both sides of each of the flexible portions 15 and 16. In the present embodiment, the individual pressure-sensitive adhesive layers 19, 19 are provided in the shape of a strip extending continuously in the longitudinal direction over almost the same length as the compressed grooves 10, 10.

In the sanitary napkin 1 before use, the pressure-sensitive adhesive layers 19, 19 are covered with and protected by a release sheet.

After the release sheet is peeled off, the sanitary napkin 1 is adhered and fixed to an inner side of a crotch portion of an undergarment through the pressure-sensitive adhesive layers 19, 19. By wearing the undergarment with the sanitary napkin 1 thus fixed thereto, the sanitary napkin 1 can be worn in the wearer's crotch.

Figure 8:
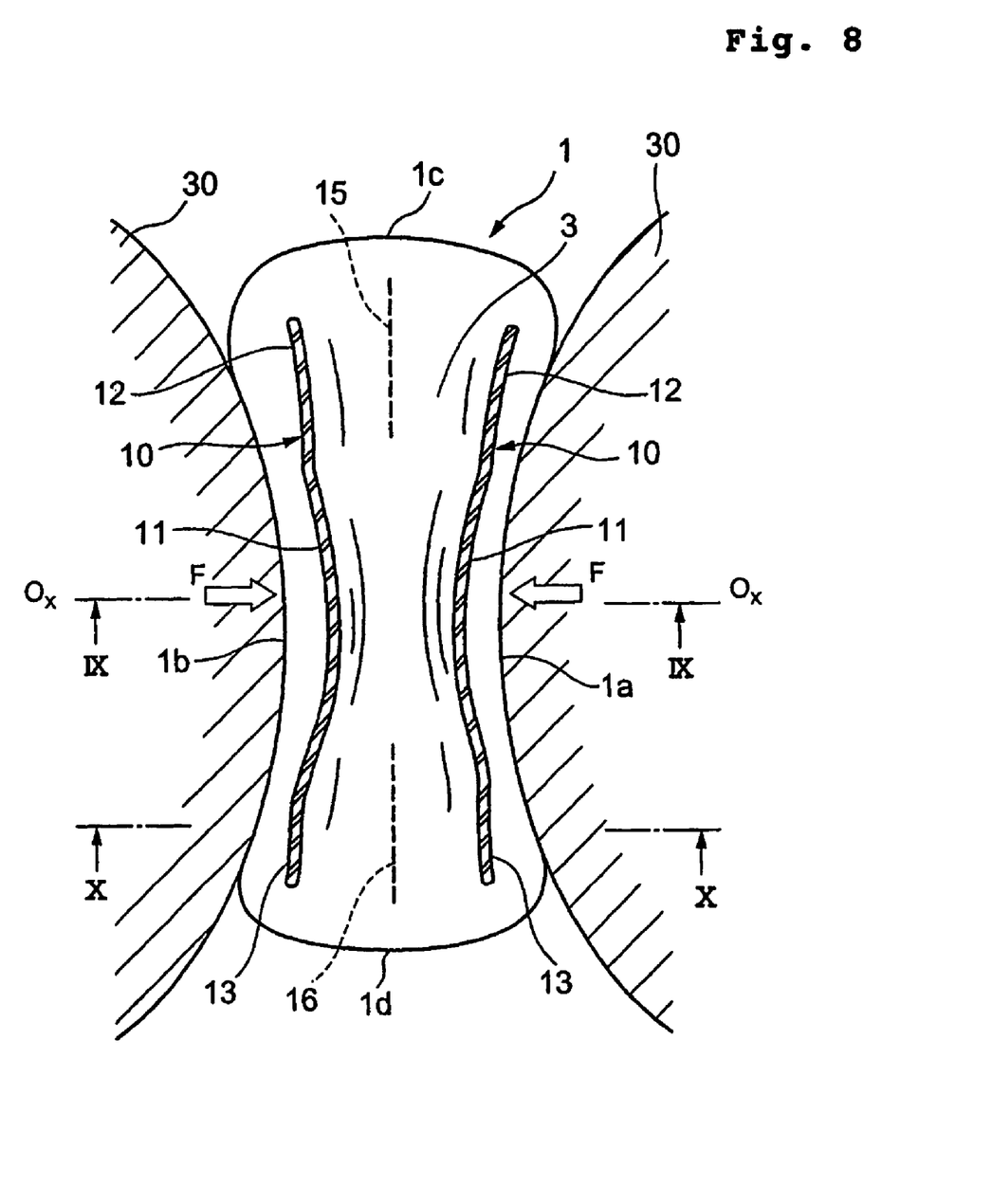
FIG. 8 is a top plan view showing a state where the sanitary napkin is applied to the crotch of a wearer.
Figure 9:
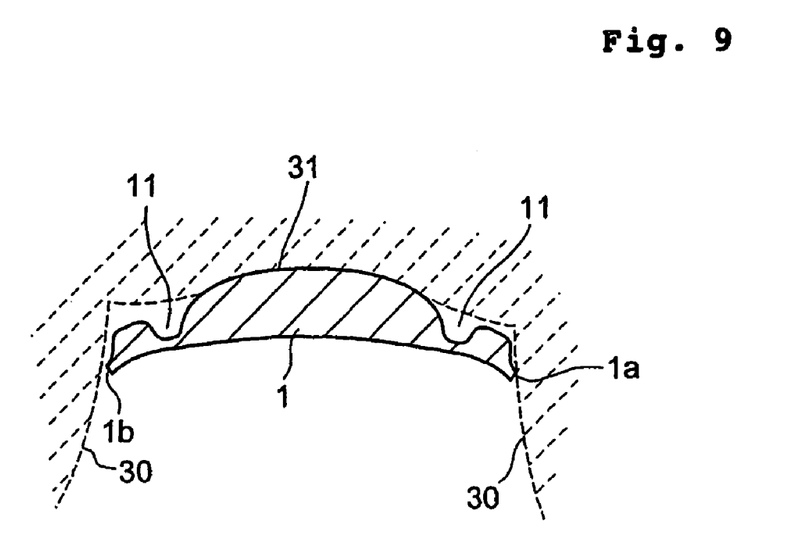
FIG. 9 is a sectional view taken along line IX-IX of FIG. 8.
Figure 10:
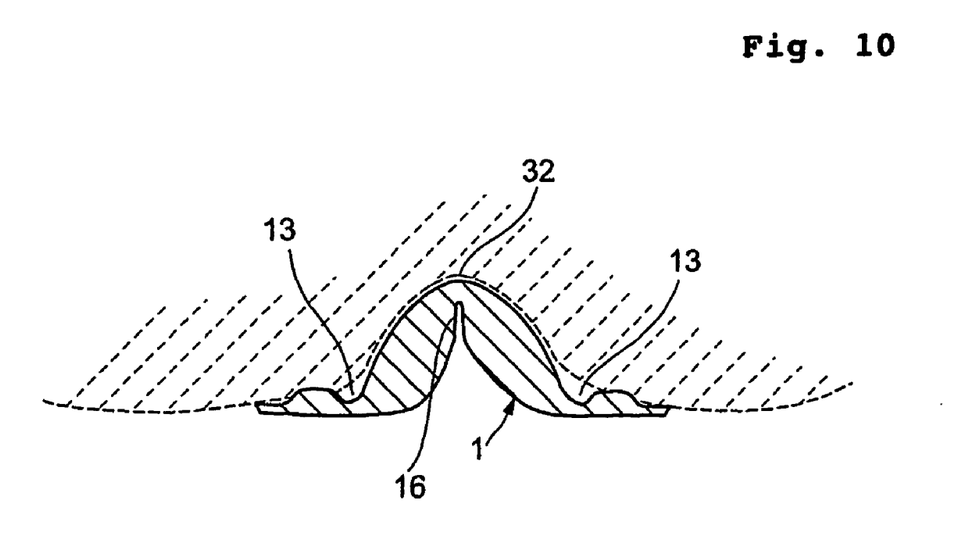
FIG. 10 is a sectional view taken along line X-X of FIG. 8.

FIG. 8 is a view showing a state in which the sanitary napkin 1 worn in the wearer's crotch is held between the thighs 30, 30 with the skin surface facing upward; FIG. 9 is a sectional view taken along line IX-IX of FIG. 8; and FIG. 10 is a sectional view taken along line X-X of FIG. 8.

The sanitary napkin 1 is to be worn with the lateral reference line Ox-Ox crossing near the center of the vaginal opening. When worn, the thighs 30, 30 exert a pressure toward the longitudinal centerline Oy-Oy on the sanitary napkin 1, as indicated by the arrows F, F. At this time, since the compressed grooves 10, 10 on two sides are of high density, the sanitary napkin 1 can be laterally compressed so that the compressed grooves 10, 10 approach each other by the pressure F, F, while being prevented from being easily bent at the compressed grooves 10, 10.

Particularly because the separation distance between the first compressed portions 11, 11 of the compressed grooves 10, 10 becomes smallest on the lateral reference line Ox-Ox and gradually increases forward and rearward therefrom, the pressure F, F from the thighs 30, 30 can be evenly distributed over the first compressed portions 11, 11, so that the first compressed portions 11, 11 can approach each other while keeping their curved shape.

In the central portion that is shown as the region of length L1 in FIG. 1, the first liquid absorbent layer 4 can be compressed to reduce its lateral dimension in a region located between the highly stiff compressed grooves 10, 10. Since the groove bottoms of the compressed grooves 10, 10 are close to the backsheet 2 of the sanitary napkin 1, when a compressive force is applied to the first liquid absorbent layer 4 from the compressed grooves 10, 10, the first liquid absorbent layer 4 in the central portion can be deformed and pushed up toward the crotch 31 of a wearer, so that the skin surface in the central portion comes into close contact with the vaginal opening and its surroundings, as shown in FIG. 9.

Because neither the flexible portion 15 nor the flexible portion 16 is located in the central portion, particularly in between the first compressed portions 11, 11, the central portion can be prevented from being folded by the pressure F, F. Therefore, when the thighs 30, 30 move away from each other, the central portion tends to return to its original shape due to resiliency of the first liquid absorbent layer 4, whereby the central portion can always be kept in close contact with the vaginal opening and its surroundings, following the motion of the thighs 30, 30.

The pressure F, F from the thighs 30, 30 intensely acts on the first compressed portions 11, 11 in the central portion, while acting weakly on the second compressed portions 12, 12 and the third compressed portions 13, 13 in the front and rear portions as compared with the central portion. However, since the first compressed portion 11, the second compressed portion 12 and the third compressed portion 13 are continuous with each other on each side of the sanitary napkin 1, the pressure acting on the first compressed portions 11, 11 can be transmitted to the second compressed portions 12, 12 and the third compressed portions 13, 13, whereby the second compressed portions 12, 12 tend to approach each other and the third compressed portions 13, 13 also tend to approach each other.

As shown in FIG. 10, since the flexible portion 16 in the rear portion is opposed to the cleft 32 (including the anus and its surroundings) of the buttocks, when a force is so exerted on the third compressed portions 13, 13 as to make them approach each other, the first liquid absorbent layer 4 is curved toward the wearer's body at an intermediate portion between the third compressed portions 13, 13 and then folded at the flexible portion 16, whereby the rear portion bulges toward the wearer's body. As a result, the portion having the flexible portion 16 fits into the cleft 32 of the buttocks.

Also in the front portion, the portion having the flexible portion 15 tends to bulge toward the wearer's body, but because the area of the wearer's body anterior to the vaginal opening, i.e., the area from the mons pubis to the lower abdomen provides a smoothly curved surface, the front portion of the sanitary napkin 1 will be pressed against the area from the mons pubis to the lower abdomen by an undergarment to conform to the smoothly curved surface.

Menstrual blood discharged from the vaginal opening is mainly applied to the central portion, passed through the topsheet 3 and the second sheet via the liquid passage holes 18, and then absorbed by the second liquid absorbent layer 5 and the first liquid absorbent layer 4. Since the sanitary napkin 1 can be in close contact with the vaginal opening and the cleft of the buttocks as shown in FIGS. 9 and 10, lateral or rearward leakage of menstrual blood from the sanitary napkin 1 can be prevented.

Since the pressure-sensitive adhesive layers 19, 19 at least on the lateral reference line Ox-Ox are located beneath the right and left compressed grooves 10, 10 as shown in FIG. 2 or near the right and left compressed grooves 10, 10, the side portions having the compressed grooves 10, 10 can be firmly fixed to an undergarment so as not to be folded back against the skin surface during wear, so that the pressure F, F from the thighs 30, 30 can be certainly transmitted from the first compressed portions 11, 11 to the first liquid absorbent layer 4, which results in bulging deformation of the first liquid absorbent layer 4 shown in FIG. 9.

Since the pressure-sensitive adhesive layers 19, 19 at both sides of the flexible portion 16 in the rear portion are also located beneath or near the third compressed portions 13, 13, the portions having the third compressed portions 13, 13 can be firmly fixed to an undergarment so as not to be twisted or folded back against the skin surface. Therefore, the flexible portion 16 will be hardly offset from the cleft 32 of the buttocks to either right or left of FIG. 10, so that the portion having the flexible portion 16 can be certainly deformed to bulge toward the cleft 32 of the buttocks.

In the central portion, as set forth above, since the flexible portions are not present between the compressed grooves 10, 10, the sanitary napkin 1 can be prevented from being sharply bent when it comes into close contact with the wearer's crotch 31 in a compressed, bulging state. In addition, the sanitary napkin 1 can be repeatedly contracted and restored to follow the motion of the thighs 30, 30. With the pressure F, F from the thighs 30, 30 being transmitted from the first compressed portions 11, 11 to the third compressed portions 13, 13, furthermore, the portion having the flexible portion 16 can be folded to fit in the cleft 32 of the buttocks, as shown in FIG. 10. Thus, the portion having the flexible portion 16 can always be kept in close contact with the cleft 32 of the buttocks.

Thus, since the sanitary napkin 1 can conform to the contour of the wearer's body with the pressure F, F from the thighs 30, 30, it is not necessarily required to use a tight undergarment in combination with the sanitary napkin 1.

In addition, since the sanitary napkin 1 is of symmetrical configuration about the lateral reference line Ox-Ox and the flexible portions 15 and 16 are symmetrical to each other about the lateral reference line Ox-Ox, the sanitary napkin 1 can be deformed as shown in FIGS. 9 and 10 regardless which one of the front and rear end edges 1c and 1d is directed forward.

Next, preferred materials for the individual components will be described.

The topsheet 3 may be through-air bonded nonwoven fabric having a basis weight of about 15 to 40 g/m$^2$, wherein sheath/core bicomponent synthetic fibers, of which the core component is polyethylene terephthalate (PET) containing titanium oxide and the sheath component is polyethylene (PE), are bonded together by means of hot air. In an alternative, the topsheet 3 may be spunbonded or spunlaced nonwoven fabric, synthetic resin film formed with a large number of liquid passage holes, or synthetic resin sheet formed in the shape of a net.

The backsheet 2 may be liquid-impermeable and air-permeable or air-impermeable sheet such as polyethylene (PE) or polypropylene (PP) film.

Although omitted from the drawings, the second sheet is provided beneath the topsheet 3 at least in the region over which the liquid passage holes 18 are distributed. The second sheet may be formed of through-air bonded nonwoven fabric comprising sheath/core bicomponent synthetic fibers, of which the core component is polypropylene (PP) and the sheath component is polyethylene (PE). The through-air bonded nonwoven fabric is used for the second sheet as it is or after folded to have a multi-layer structure and the resultant second sheet has a basis weight of about 15 to 40 g/m$^2$. Since the fibers of the second sheet are bonded together to provide a three-dimensional network structure to leave many voids inside the second sheet, menstrual blood having passed through the topsheet 3 can fall through the voids under gravitation for subsequent absorption by the second liquid absorbent layer 5 or the first liquid absorbent layer 4.

The first liquid absorbent layer 4 may be formed by adding synthetic absorbent polymer such as polyacrylate, polyacrylamide and maleic anhydride or natural absorbent polymer such as starch and cellulose to an aggregate of pulp such as ground pulp, mercerized pulp or crosslinked pulp, wherein the pulp and the synthetic absorbent polymer or the like are wrapped in hydrophilic tissue paper.

The second liquid absorbent layer 5 may be air-laid nonwoven fabric (air-laid pulp), in which 60-80 wt. % of ground pulp and synthetic fibers are accumulated by an air-laid process and the fibers are bonded together using about 4-8 wt. % of binder. In an alternative, the second liquid absorbent layer 5 may be air-laid pulp not containing synthetic fibers.

In the present embodiment, the liquid absorbent layer is formed by laying the second liquid absorbent layer 5 on the first liquid absorbent layer 4, but should not be construed as limited to such a two-layer structure. It is, of course, possible that the liquid absorbent layer be of a single-layer structure.

The first liquid absorbent layer 4 manufactured by wrapping pulp and so on in tissue paper is preferably compressed as a whole prior to assembly to the other components, wherein the flexible portions 15 and 16 can be formed in the same compression step. Alternatively, the flexible portions 15 and 16 may be formed in a step different from the compression step.

Figure 5:
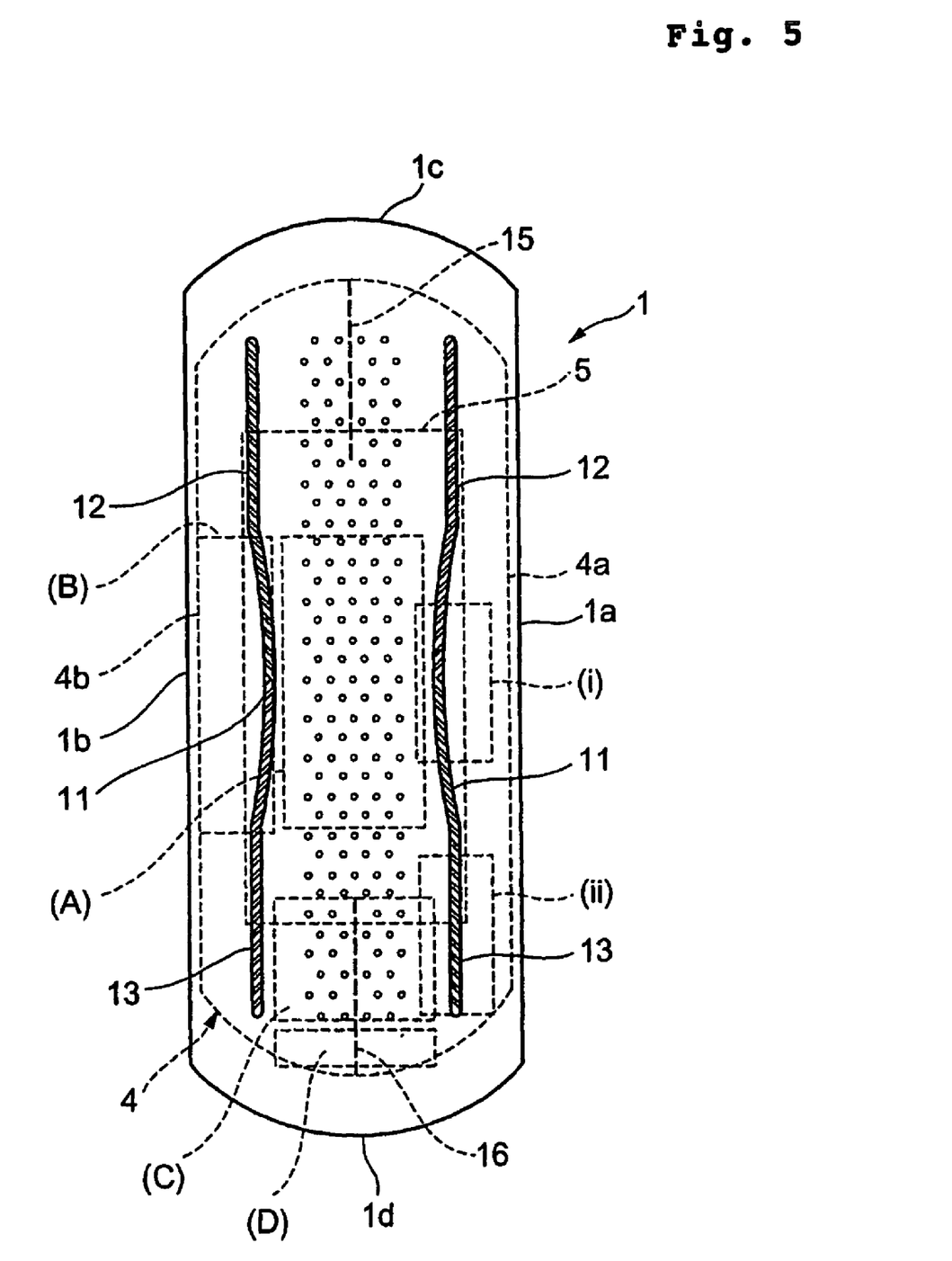
FIG. 5 is a top plan view which is similar to FIG. 1 and to be used for describing properties of respective portions.

FIG. 5 is a top plan view of the sanitary napkin 1, which is similar to FIG. 1 and to be used for describing properties of respective portions.

FIG. 5 shows a first region (A), a second region (B), a third region (C) and a fourth region (D). The first region (A) is positioned in the central portion and between the first compressed portions 11, 11. The second region (B) is also positioned in the central portion but outside the first region (A) to have one of the first compressed portions 11, 11 therein. More specifically, the second region (B) extends laterally from the first compressed portion 11 on the left side to the left side edge 4b of the first liquid absorbent layer 4. The third region (C) is positioned between the third compressed portions 13, 13 and within the range over which the flexible portion 16 overlaps with the third compressed portions 13, 13 as viewed from the lateral direction. The fourth region (D) is positioned rearward of the third compressed portions 13, 13 and provided with the first liquid absorbent layer 4. Here, the range of the first region (A) should not be construed as limited to the area surrounded by a dotted line in FIG. 5, but the first region (A) positioned between the compressed grooves 10, 10 may extend over the length L1 at the maximum.

It should be noted that since the sanitary napkin 1 is of symmetrical configuration about the lateral reference line Ox-Ox, the third region (C) and the fourth region (D) are also provided in the front portion of the sanitary napkin 1. Of course, the second region (B) is also provided in the right side of the sanitary napkin 1.

In the first region (A), the first and second liquid absorbent layers 4 and 5 have high mean basis weights and the sanitary napkin 1 has a high mean thickness. In the second region (B), the first liquid absorbent layer 4 (the second liquid absorbent layer 5 overlaps with the second region (B) as shown in FIG. 5) has a lower mean basis weight and the sanitary napkin 1 has a lower mean thickness than in the first region (A). Also in the third region (C), the first liquid absorbent layer 4 (the second liquid absorbent layer 5 overlaps with the third region (C) as shown in FIG. 5) has a lower mean basis weight and the sanitary napkin 1 has a lower mean thickness than in the first region (A). In the fourth region (D), the first liquid absorbent layer 4 has a much lower mean basis weight and the sanitary napkin 1 has a much lower mean thickness than in the third region (C).

With the basis weight and the thickness increased in the first region (A), the first liquid absorbent layer 4 can be prevented from being sharply bent even when subjected to the pressure F, F from the thighs 30, 30, so that the skin surface can be curved to bulge and come into close contact with the wearer's crotch 31, as shown in FIG. 9. Here, the means basis weight in the first region (A) is preferably in the range of 400 to 1000 g/m$^2$. If it is in excess of the above-mentioned range, the first and second liquid absorbent layers 4 and 5 after shaping by compression will be excessively stiff, giving an unpleasant feeling to the thighs 30 and so on. If it is below the above-mentioned range, on the other hand, the menstrual blood absorption capacity will be excessively decreased and the stiffness will be decreased to cause excessive contraction in the lateral direction when subjected to the pressure F, F. In addition, it will be hardly restored to its original shape even when the pressure F, F from the thighs 30, 30 decreases. The basis weight in the first region (A) is more preferably in the range of 600 to 800 g/m$^2$.

With the mean basis weight and the mean thickness in the second region (B) being slightly lower than those in the first region (A), the density and stiffness of the first compressed portions 11, 11 can be appropriately adjusted. The means basis weight in the second region (B) is preferably in the range of 400 to 800 g/m².

If it is below the above-mentioned range, the density and stiffness of the first compressed portions 11, 11 will be excessively decreased, so that the lateral pressure F, F can not be suitably received by the first compressed portions 11, 11 for deformation of the first liquid absorbent layer 4 into the state shown in FIG. 9. If the stiffness of the first compressed portions 1, 11 is excessively decreased, furthermore, a deforming force due to the pressure F, F cannot be efficiently transmitted to the second compressed portions 12, 12 and the third compressed portions 13, 13, so that the rear portion cannot be certainly deformed into the state of FIG. 10 only by the pressure F, F. If it is in excess of the above-mentioned range, on the other hand, the stiffness of the first compressed portions 11, 11 will be excessively increased, making deformation of the first compressed portions 11, 11 due to the lateral pressure F, F difficult to occur, as well as giving an unpleasant feeling to the thighs 30, 30.

With the mean basis weight in the third region (C), in which the flexible portion 16 overlaps with the third compressed portions 13, 13 as viewed from the lateral direction, being lower than that in the first region (A), the third region (C) can be easily deformed into the state of FIG. 10.

The means basis weight in the third region (C) is preferably in the range of 300 to 600 g/m². If it is below the above-mentioned range, the stiffness of the third region (C) will be excessively decreased, so that even if a force to make the third compressed portions 13, 13 approach each other is exerted, the third region (C) cannot be easily deformed into the state of FIG. 10 and even after deformation, the third region (C) thud deformed to bulge will be easily flattened out by pressure from the wearer s body. If it is in excess of the above-mentioned range, the stiffness of the first liquid absorbent layer 4 deformed into the state of FIG. 10 will be excessively increased, giving an unpleasant feeling to the buttocks.

In the fourth region (D), on the other hand, the third compressed portions 13, 13 are not located at two sides of the flexible portion 16. Accordingly, if the mean basis weight and the mean thickness in the fourth region (D) are equal to those in the third region (C), it will be difficult to make the fourth region (D) bulge as shown in FIG. 10 only with the force transmitted to the third compressed portions 13, 13 to make them approach each other. In the present embodiment, however, since the mean basis weight and the mean thickness in the fourth region (D) are sufficiently decreased, the fourth region (D) can also be easily deformed to bulge, following the deformation of the third region (C) into the state of FIG. 10. To this end, the means basis weight in the fourth region (D) is preferably in the range of 200 to 400 g/m².

The compressed grooves 10, 10 have a width of 1.5 to 4 mm. In the arrangement direction, the high-density compressed portions 10a have a dimension of 0.4 to 1.0 mm while the medium-density compressed portions 10b have a dimension of 2.0 to 5.0 mm, wherein the high-density compressed portions 10a are preferably arranged at a pitch of 2.4 to 6.0 mm. It is also preferred that the high-density compressed portions 10a have a density of at least 0.4 g/cm³ and that the medium-density compressed portions 10b have a density of at least 0.1 g/cm³.

FIG. 5 also shows a first measuring region (i) that is traversed by the first compressed portion 11 and a second measuring region (ii) that is traversed by the third compressed portion 13. It is preferred that the first measuring region (i) has a Gurley stiffness of 14 to 40 mN and that the second measuring region (ii) has a Gurley stiffness of 10 to 25 mN. Of course, the corresponding region that is traversed by the second compressed portion 12 in the front portion has the same Gurley stiffness as the second measuring region (ii).

The Gurley stiffnesses can be measured by using a Gurley Flexibility Tester manufactured by YASUDA SEIKI SEISAKUSHO, LTD, wherein the individual measuring regions have a width of 25 mm in the lateral direction and a length of 38 mm in the longitudinal direction. The measurements of the Gurley stiffness are made in such a manner that after the first and second measuring regions (i) and (ii) are cut out of the sanitary napkin 1 in the above-mentioned dimensions, bending test is performed with each sample brought into contact with a pendulum of the Gurley Flexibility Tester within a length of 6.3 mm from one longitudinal end edge while being held by a chuck within a length of 6.3 mm from the other end edge. The average of the value measured for one bending direction in which the skin surface is pushed and the value measured for the other bending direction in which the garment surface is pushed is taken as the Gurley stiffness.

With the compressed grooves 10 thus formed and with the Gurley stiffnesses of the measuring regions thus set in the above-mentioned ranges, the first liquid absorbent layer 4 can be easily deformed into the state of FIG. 9 in the central portion by the pressure F, F acting on the first compressed portions 11, 11. In addition, an unpleasant feeling will not be given to the wearer's crotch. With the stiffnesses thus set, furthermore, the compressive force transmitted from the first compressed portions 11, 11 to the third compressed portions 13, 13 can be effectively exerted on the flexible portion 16, facilitating the deformation of the rear portion into the state of FIG. 10. Still furthermore, the sanitary napkin 1 can be prevented from being folded or excessively twisted at the compressed grooves 10, 10.

The minimum separation distance between the compressed grooves 10, 10, i.e., the separation distance between the first compressed portions 11, 11 on the lateral reference line Ox-Ox is preferably in the range of 20 to 45 mm. If it is below the above-mentioned range, it will be difficult to cover the vaginal opening with the portion between the first compressed portions 11, 11. If it is in excess of the above-mentioned range, the first liquid absorbent layer 4 subjected to the pressure F, F from the thighs 30, 30 will be excessively bulged between the compressed portions 11, 11 toward the wearer's crotch and will be easily flattened out by a pressure applied from the wearer's crotch.

The maximum separation distance between the compressed grooves 10, 10, i.e., the separation distance between the second compressed portions 12, 12 and between the third compressed portions 13, 13 is preferably in the range of 45 to 60 mm. If it is below the above-mentioned range, the slope of the bulging skin surface when deformed as shown in FIG. 10 will be too steep to fit in the cleft of the buttocks; if it is in excess of the above-mentioned range, on the other hand, the slope will be too gentle to fit in the cleft of the buttocks.

The flexible portions 15 and 16 have a width of 0.5 to 4.0 mm, and the thickness of the first liquid absorbent layer 4 at the flexible portions 15 and 16 is preferably at most ⅔, more preferably at most ½ of that at portions of the third region (C) other than the flexible portion 16. With the flexible portions 15 and 16 thus formed, the first liquid absorbent layer 4 can be easily deformed to bulge as shown in FIG. 10 by pressure transmitted to the second compressed portions 12, 12 or the third compressed portions 13, 13.

The distance (L1/2) from the starting points 15a and 16a of the flexible portions 15 and 16 to the lateral reference line Ox-Ox is preferably in the range of 30 to 60 mm. If it is below the above-mentioned range, the central portion extending over the length L1 will be bent as shown in FIG. 10, making the contact of the skin surface of the sanitary napkin 1 with the wearer's crotch unstable and decreasing an elastic restoring force to be produced by the central portion when the pressure F, F from the thighs 30, 30 is reduced.

It is preferred that the flexible portions 15 and 16 extend over at least ½ the distance between the starting point 15a to the front end edge 1c and the distance between the starting point 16a to the rear end edge 1d, respectively. If not, it will be difficult to cause the bulging deformation for fitting in the cleft of the buttocks as shown in FIG. 10.

It is preferred that as viewed from the lateral direction, the pressure-sensitive adhesive layers 19, 19 overlap with the flexible portions 15 and 16 over at least ⅔ the length of the flexible portions 15 and 16. Within this range, both side regions of each of the flexible portions 15 and 16 can be firmly fixed to an undergarment, so that the rear portion can be easily deformed into the state of FIG. 10. It is also preferred that the second compressed portions 12, 12 do not project more than 5 mm forward beyond front ends 19a, 19a of the pressure-sensitive adhesive layers 19, 19 and the third compressed portions 13, 13 do not project more than 5 mm rearward beyond rear ends 19b, 19b of the pressure-sensitive adhesive layers 19, 19, either.

As shown in FIG. 2, the pressure-sensitive adhesive layers 19, 19 are preferably disposed to overlap with the compressed grooves 10, 10. If the pressure-sensitive adhesive layers 19, 19 do not overlap with the compressed grooves 10, 10, it is preferred that the pressure-sensitive adhesive layers 19, 19 are not located more than 5 mm apart from the compressed grooves 10, 10 in the lateral direction.

With the pressure-sensitive adhesive layers 19, 19 thus disposed, the sanitary napkin 1 can be firmly fixed to an undergarment at the portions having the compressed grooves 10, 10, whereby the portions having the compressed grooves 10, 10 can be prevented from being folded back against the skin surface and the first liquid absorbent layer 4 can be certainly deformed as shown in FIGS. 9 and 10 through the compressed grooves 10, 10.

Figure 6:
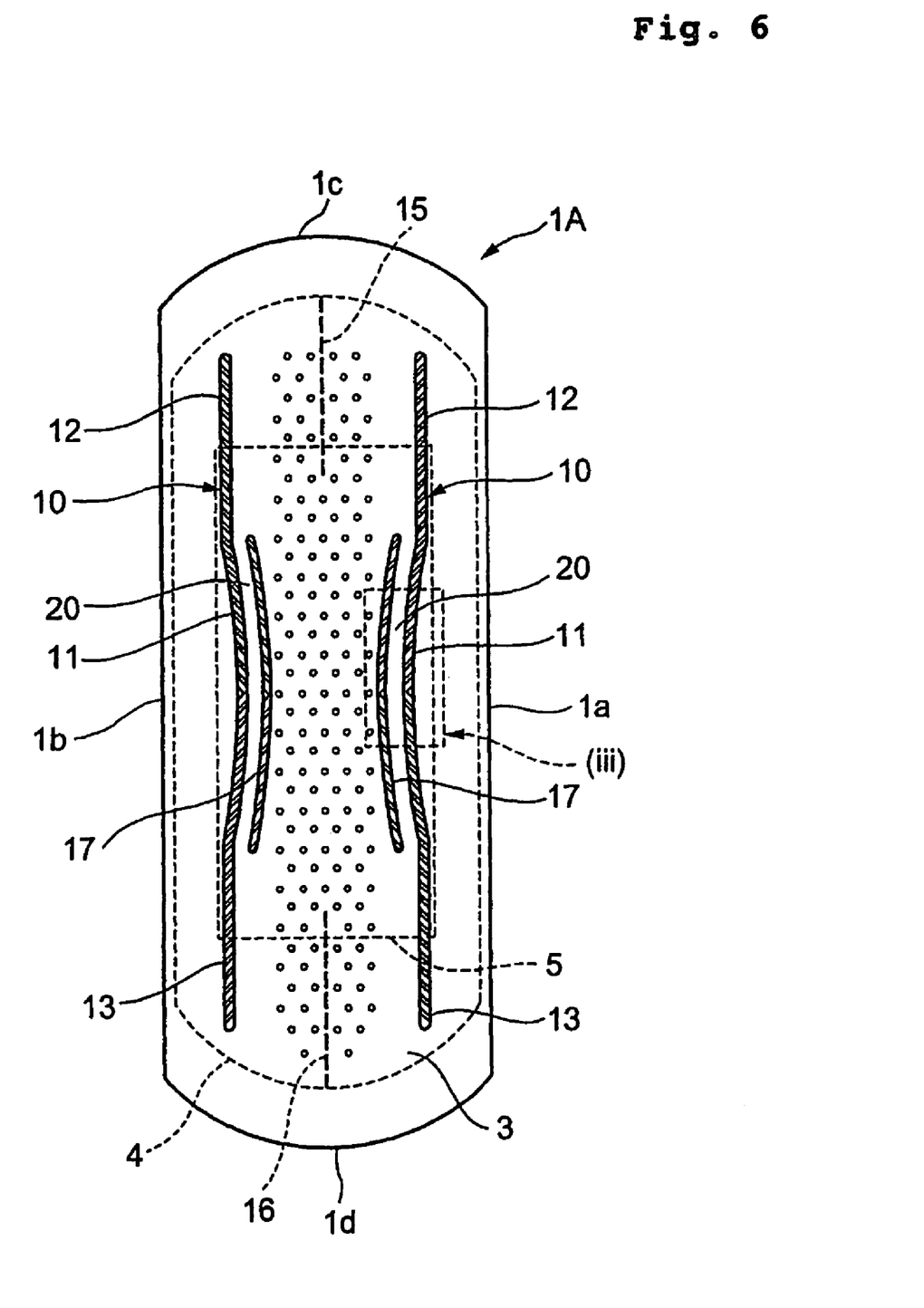
FIG. 6 is a top plan view showing a sanitary napkin as an absorbent article according to a second embodiment of the present invention.

FIG. 6 is a top plan view showing a sanitary napkin 1A as an absorbent article according to a second embodiment of the present invention.

In the sanitary napkin 1A, inner compressed grooves 17, 17 are formed inside the first compressed portions 11, 11 of the compressed grooves 10, 10. The inner compressed grooves 17, 17 are formed in the same manner as the compressed grooves 10, 10, so that the high-density compressed portions 10a and the medium-density compressed portions 10b alternate with each other and the skin surface is recessed toward the garment surface. Preferred ranges of the dimension and density of the inner compressed grooves 17, 17 are identical to those of the compressed grooves 10, 10.

The inner compressed grooves 17, 17 are formed to extend over substantially the same length as the first compressed portions 11, 11 in the longitudinal direction. The inner compressed grooves 17, 17 are curved toward the longitudinal centerline Oy-Oy. On each side, the center of curvature of the inner compressed groove 17 almost coincides with the center of curvature of the first compressed portion 11, so that the distance between the inner compressed groove 17 and the first compressed portion 11 is constant everywhere. Since the first compressed portions 11, 11 and the inner compressed grooves 17, 17 are formed adjacent each other by simultaneous pressing, furthermore, high-density portions 20, 20 where the first liquid absorbent layer 4 is compressed to some degree are formed between the first compressed portions 11, 11 and the inner compressed grooves 17, 17.

In the sanitary napkin 1A subjected to the pressure F, F from the thighs 30, 30, since the first liquid absorbent layer 4 is strongly compressed from both sides in the central portion due to the presence of the first compressed portions 11, 11, the inner compressed grooves 17, 17 and the high-density portions 20, 20, the first liquid absorbent layer 4 can be easily deformed to bulge in the central portion as shown in FIG. 9. In addition, since the first compressed portions 11, 11, the inner compressed grooves 17, 17 and the high-density portions 20, 20 tend to deform to approach the longitudinal centerline Oy-Oy all together when applied the pressure F, F, the deforming force can be easily transmitted from these portions to the second compressed portions 12, 12 and the third compressed portions 13, 13. In the rear portion, therefore, the portion having the flexible portion 16 can be easily deformed to bulge toward the cleft 32 of the buttocks.

It should be noted that also in FIG. 6, the contour of the sanitary napkin 1A and the pattern of the compressed grooves 10, 10 and the inner compressed grooves 17, 17 are symmetrical about the lateral reference line Ox-Ox. The separation distance between the inner compressed grooves 17, 17 becomes smallest, preferably in the range of 20 to 45 mm, on the lateral reference line Ox-Ox. FIG. 6 shows a measuring region (iii) that is traversed by both the first compressed portion 11 and the inner compressed groove 17. Preferred range of the Gurley stiffness of the measuring region (iii) is equal to that of the measuring region (i) of the sanitary napkin 1 according to the first embodiment shown in FIG. 5.

Figure 7:
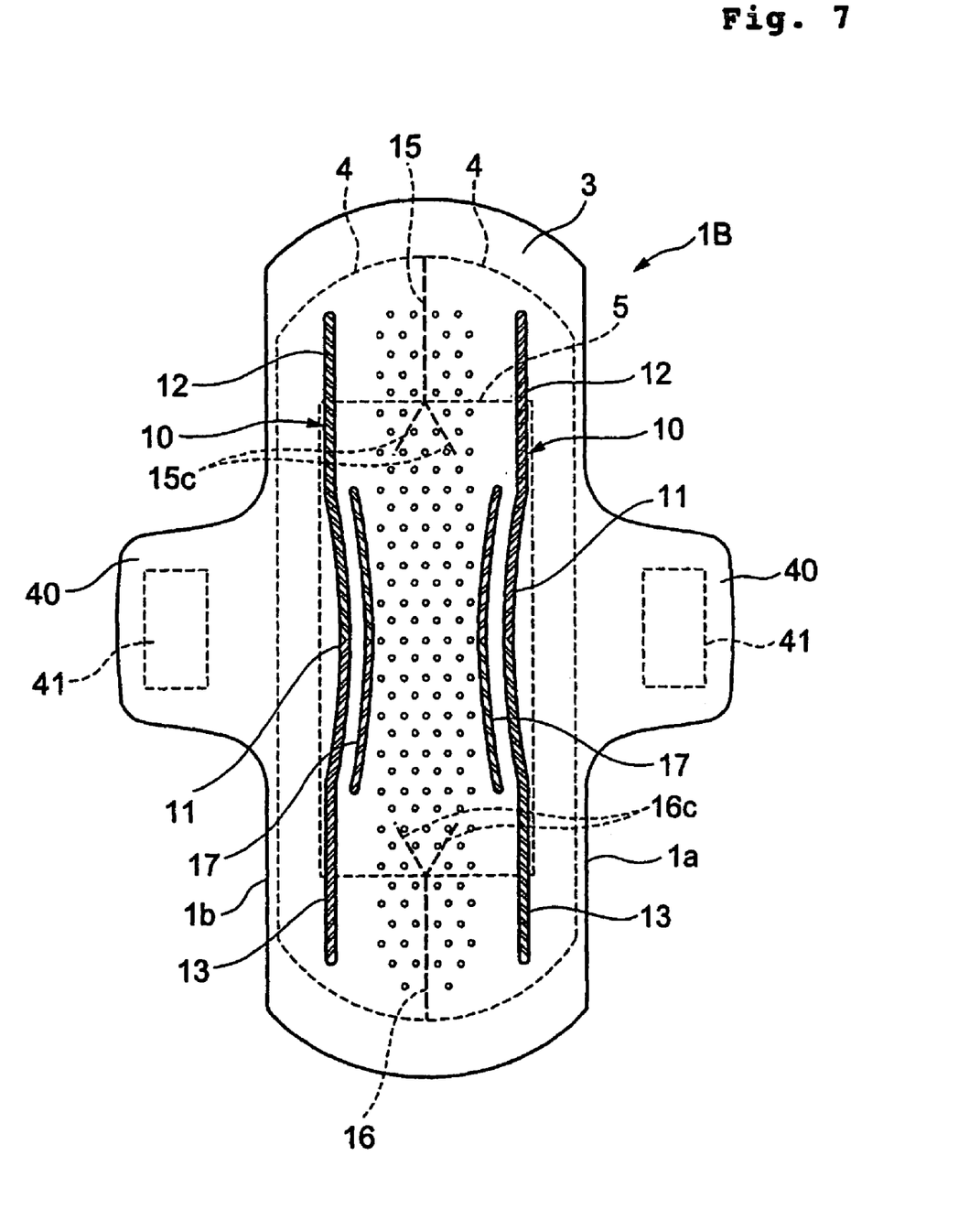
FIG. 7 is a top plan view showing a sanitary napkin as an absorbent article according to a third embodiment of the present invention.

FIG. 7 is a top plan view showing a sanitary napkin 1B according to a third embodiment of the present invention. The sanitary napkin 1B has the same basic structure as the sanitary napkin 1A according to the second embodiment. However, the right side edge 1a and the left side edge 1b are projected to right and left with center at the lateral reference line Ox-Ox, thereby forming wings 40, 40. On the back side of the wings 40, 40, there are disposed pressure-sensitive adhesive layers 41, 41.

The sanitary napkin 1B is worn such that after adhered to an inner side of a crotch portion of an undergarment through the pressure-sensitive adhesive layers 19, 19, the wings 40, 40 are folded back against an outer side of the crotch portion of the undergarment to cover both side edges of the crotch portion and then adhered to the outer side of the crotch portion through the pressure-sensitive adhesive layers 41, 41.

In the sanitary napkin 1B, the flexible portion 15 is bifurcated at one end directed to the lateral reference line Ox-Ox to provide bifurcated flexible portions 15c, 15c. Likewise, the flexible portion 16 is bifurcated at one end directed to the lateral reference line Ox-Ox to provide bifurcated flexible portions 16c, 16c. The bifurcated flexible portions 15c, 15c may be continuous with or separated from the flexible portion 15 and the bifurcated flexible portions 16c, 16c may also be continuous with or separated from the flexible portion 16.

Since the bifurcated flexible portions 15c, 15c and the bifurcated flexible portions 16c, 16c are directed as shown in FIG. 7, when the rear portion is bent at the flexible portion 16 to bulge as shown in FIG. 10, the deformation hardly affects the central portion. Thus, the central portion can be prevented from being sharply bent.

This sanitary napkin 1B is also of symmetrical configuration about the lateral reference line Ox-Ox.

The wings 40, 40 may also be provided in the embodiments shown in FIGS. 1 and 6. Also in the embodiments shown in FIGS. 1 and 6, the flexible portions 15 and 16 may be bifurcated to have the bifurcated flexible portions 15c, 15c and 16c, 16c, respectively. As in the third embodiment, the bifurcated flexible portions 15c, 15c may be continuous with or separated from the flexible portion 15 and the bifurcated flexible portions 16c, 16c may also be continuous with or separated from the flexible portion 16.

Although the present invention has been illustrated and described with respect to exemplary embodiments thereof, it should be understood by those skilled in the art that the foregoing and various other changes, omission and additions may be made therein and thereto, without departing from the spirit and scope of the present invention. For example, although the sanitary napkins according to the foregoing embodiments are all symmetrical about the lateral reference line Ox-Ox, a portion located rearward of the lateral reference line Ox-Ox may be longer than a portion located forward of the lateral reference line Ox-Ox. Also in this construction, with the flexible portion 16 being located between the third compressed portions 13, 13 in the rear portion, the portion having the flexible portion 16 can be deformed to fit in the cleft of the buttocks.

Therefore, the present invention should not be understood as limited to the specific embodiments set out above but to include all possible embodiments which can be embodied within a scope encompassed and equivalent thereof with respect to the feature set out in the appended claims.

INDUSTRIAL APPLICABILITY

According to the present invention, as has been described hereinabove, a central portion of the absorbent article can be brought into close contact with the wearer's crotch without being sharply bent, while a rear portion of the absorbent article can be deformed to fit in the cleft of the buttocks following the deformation of the central portion. Therefore, the absorbent article can be kept in close contact with the wearer's crotch even without wearing a tight undergarment.

The invention claimed is:

1. An absorbent article comprising
a liquid absorbent layer, the absorbent article having a skin surface and a garment surface;
a pair of compressed grooves, where the liquid absorbent layer is compressed and recessed from a side of the skin surface toward the garment surface, being provided to extend in a longitudinal direction of the article, the compressed grooves being located laterally apart from a longitudinal centerline of the article, each one of the pair of grooves being located on a single side of the longitudinal centerline, the pair of grooves each curving inwardly within a range of an equal distance forward and rearward from a lateral reference line in the longitudinal direction such that a separation distance between the compressed grooves is smallest at a point within the range, the pair of grooves being substantially parallel to each other over distances forward and rearward of the range; and
a rear flexible portion, where the liquid absorbent layer is recessed from the side of the garment surface toward the skin surface, being provided to extend toward a rear end edge of the article from a starting point that is located closer to the rear end edge than the lateral reference line, at least a portion of the rear flexible portion being located on the longitudinal centerline and between the substantially parallel compressed grooves, and
a front flexible portion, where the liquid absorbent layer is also recessed from the side of the garment surface toward the skin surface, the front flexible portion extending toward a front end edge of the article from a starting point that is located closer to the front end edge than the lateral reference line, at least a portion of the front flexible portion being located between the compressed grooves, and
the front and rear end edges are located an equal distance apart from the lateral reference line, and the front and rear flexible portions are also located an equal distance apart from the lateral reference line.

2. An absorbent article as set forth in claim 1, wherein the compressed grooves and the front and rear flexible portions are formed in a pattern symmetrical about the lateral reference line.

3. An absorbent article as set forth in claim 1, wherein within the range of an equal distance forward and rearward from the lateral reference line in the longitudinal direction, additional compressed grooves are provided side by side with the compressed grooves.

4. An absorbent article as set forth in claim 1, wherein a mean thickness of the absorbent article at both sides of the rear flexible portion is smaller than that at a region extending an equal distance forward and rearward from lateral reference line in the longitudinal direction but not overlapping with the rear flexible portion.

5. An absorbent article as set forth in claim 1, wherein pressure-sensitive adhesive layers for adhering the article to an undergarment are disposed on the garment surface, the pressure-sensitive adhesive layers being located laterally apart from the longitudinal centerline and present at least on the lateral reference line and on both sides of the rear flexible portion.

* * * * *